United States Patent [19]

Typpo

[11] Patent Number: 4,748,400
[45] Date of Patent: May 31, 1988

[54] METHOD FOR CONTROLLING THE AMOUNT OF MOISTURE ASSOCIATED WITH A WEB OF MOVING MATERIAL

[75] Inventor: Pekka M. Typpo, Cupertino, Calif.

[73] Assignee: Impact Systems, Inc., San Jose, Calif.

[21] Appl. No.: 4,989

[22] Filed: Jan. 20, 1987

[51] Int. Cl.⁴ .............................................. G01R 27/26
[52] U.S. Cl. .................................. 324/61 R; 73/1 R; 73/74
[58] Field of Search ............. 324/61 R, 61 P; 73/1 R, 73/74, 73

[56] References Cited

U.S. PATENT DOCUMENTS

| | | | |
|---|---|---|---|
| 3,535,630 | 10/1970 | McMullen | 324/61 R |
| 3,847,730 | 11/1974 | Doering | 73/73 X |
| 4,621,228 | 11/1986 | Toki et al. | 324/61 R |

*Primary Examiner*—Reinhard J. Eisenzopf
*Assistant Examiner*—Robert W. Mueller
*Attorney, Agent, or Firm*—Flehr, Hohbach, Test, Albritton & Herbert

[57] ABSTRACT

A moisture measurement and control system controlling the amount of moisture in paper being manufactured by papermaking machinery, for example, linerboard, utilizes a standard scanning moisture sensor to calibrate a nonscanning moisture sensor to thus provide very fast and accurate moisture measurements for each zone of the moving paper. The measurement is communicated to a fast response time moisture profiler, for example, of the quartz heater type. In addition, the nonscanning moisture measurement unit, which utilizes capacitive electrodes, has improved accuracy due to its electrode arrangement and signal processing technique.

5 Claims, 5 Drawing Sheets

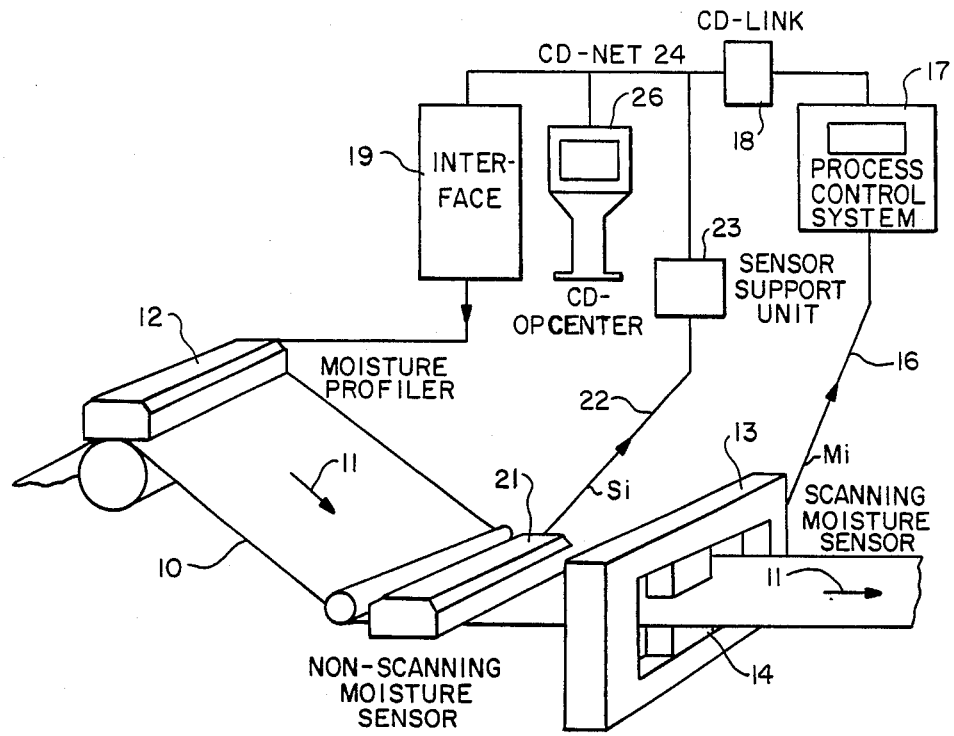
FIG.—1
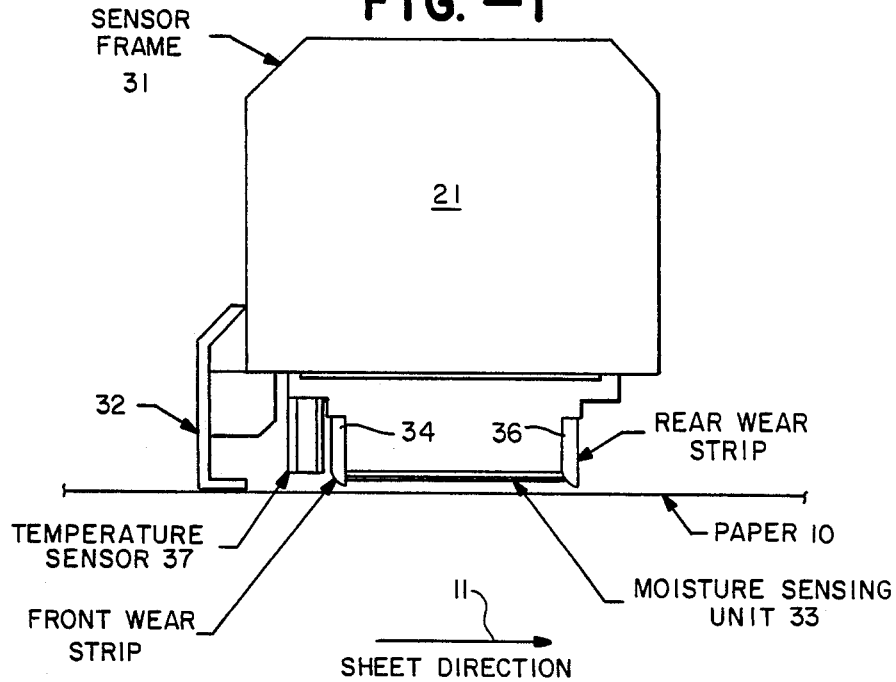
FIG.—2

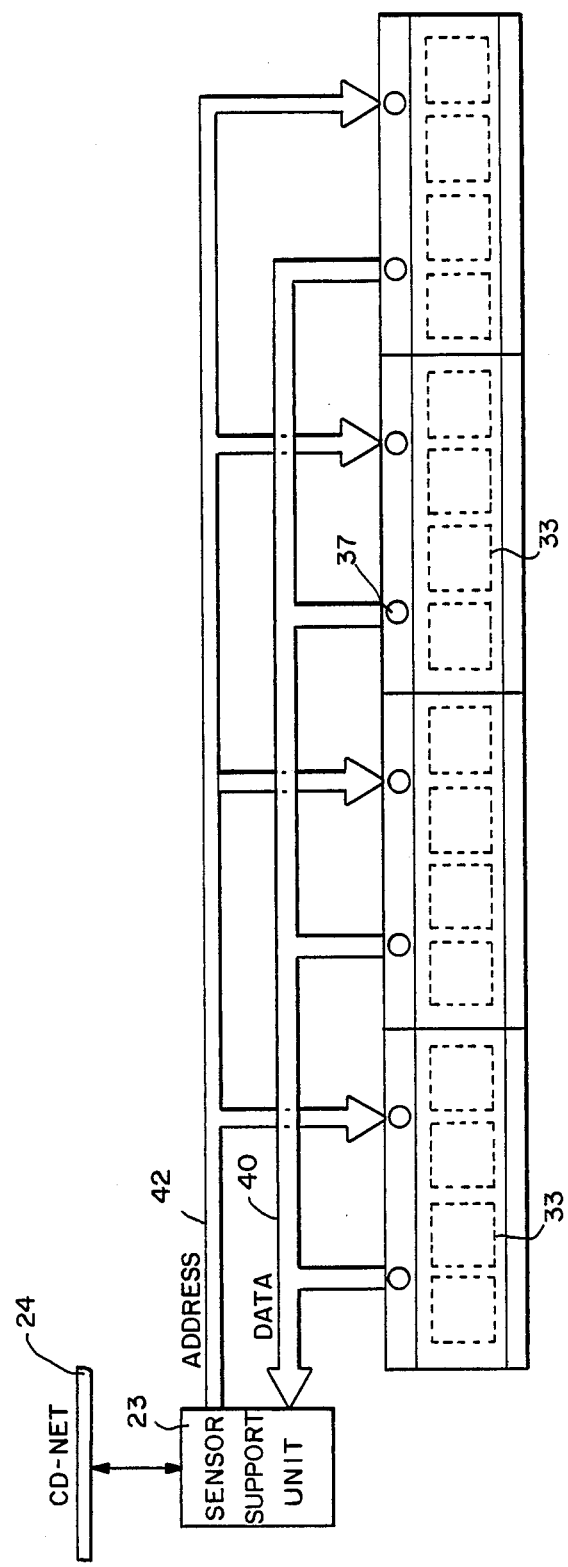
FIG.—3

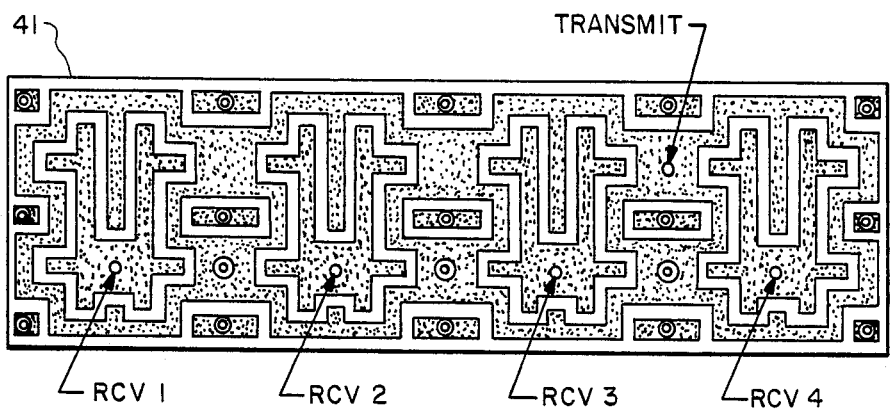
FIG.—4
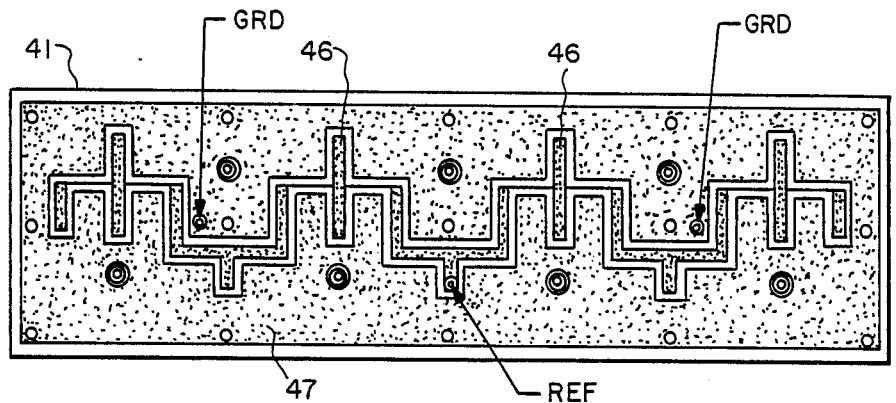
FIG.—5
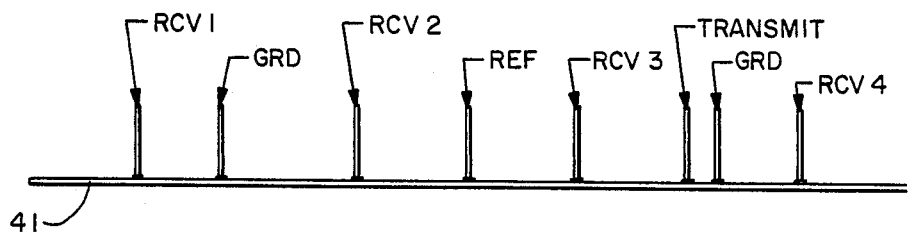
FIG.—6

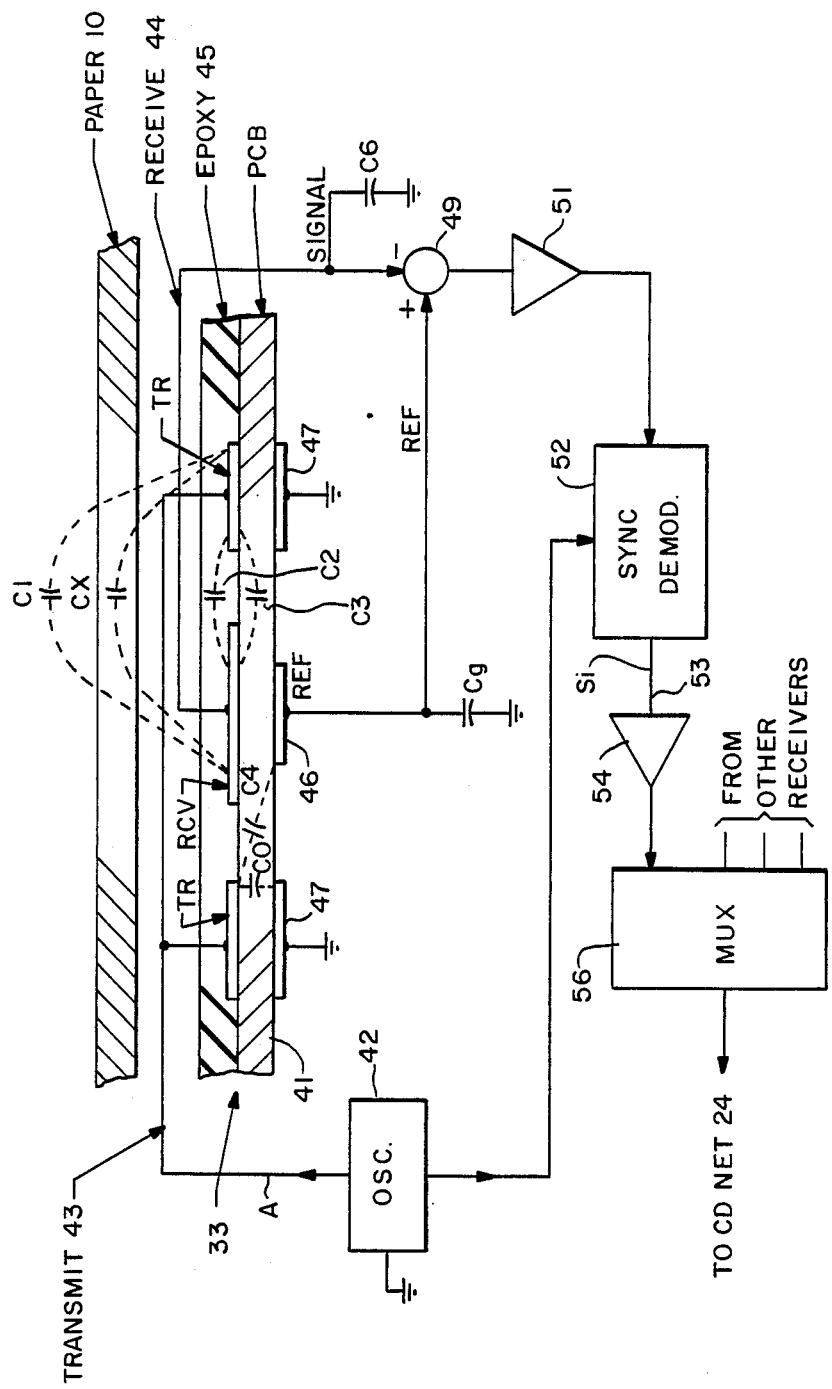
FIG.—7

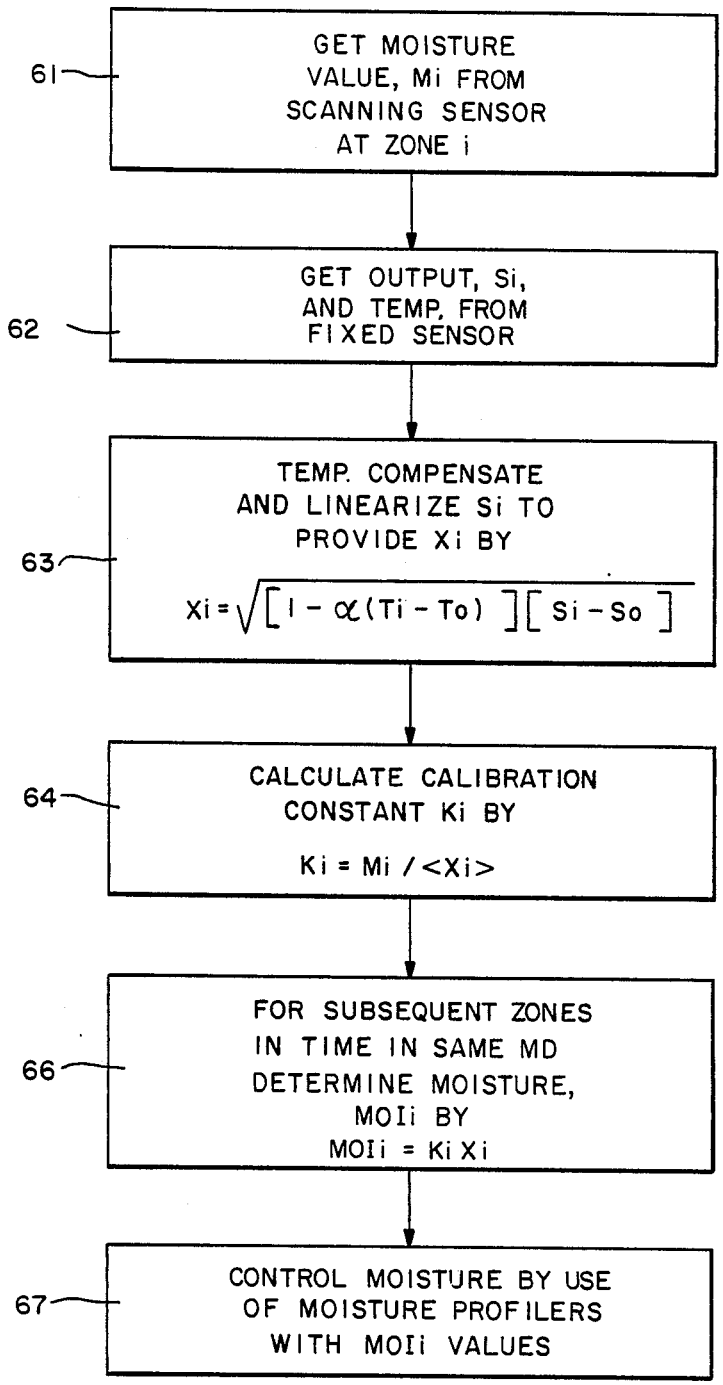
FIG.—8

METHOD FOR CONTROLLING THE AMOUNT OF MOISTURE ASSOCIATED WITH A WEB OF MOVING MATERIAL

BACKGROUND OF THE INVENTION

The present invention relates generally to a method for controlling the amount of moisture that is associated with a web of moving material and more specifically, to a method utilizing a fixed moisture sensor having a very fast response time.

DESCRIPTION OF THE PRIOR ART

The measurement of moisture in a moving web of, for example, paper, is presently being done by a scanning type moisture sensor utilizing an infrared frequency which is sensitive to the moisture in the paper. Although such sensor provides very accurate moisture values, in part because of the use of off-sheet standardization, its inherent nature due to the fact that it must scan means that there is a significant time delay between moisture measurements. For example, as much as thirty seconds between the measurement of moisture on each zone or slice of the moving paper can occur. When a type of sheet material, such as linerboard is being manufactured which may have rapid variations in moisture content, it is desirable to readjust the moisture content in a relatively short time—for example, two seconds. This can theoretically be accomplished by the use of modern day moisture profilers which utilize, for example, electrical heating elements of the quartz type to control the moisture content of the moving web. Such a type is manufactured by the assignee of the present invention under the trademark "INFRAPAC" and is illustrated in U.S. Pat. No. 4,573,402.

Nonscanning moisture sensors are, of course, known such as that manufactured by Eur-Control of Sweden. This is a moisture sensor designed for use on a stand alone basis, to in effect replace the scanning moisture sensor. However, it is believed that its accuracy is relatively poor compared to the scanning moisture sensor. The capacitive type of sensor shown in the Eur-Control device is also illustrated in U.S. Pat. Nos. 3,408,566 and 3,684,953 assigned to Industrial Nucleonics Corporation.

OBJECTS AND SUMMARY OF INVENTION

It is therefore an object of the present invention to provide an improved method for controlling the amount of moisture that is associated with a web of moving material.

It is a more specific object to provide a method as above, which provides a rapid response time to measured moisture.

In accordance with the above objects, there is provided a method using a fixed moisture sensor for controlling the amount of moisture that is associated with a web of moving material where a scanning moisture sensors scans across zones or slices of the web in a cross direction perpendicular to the machine direction of movement of the web. This provides, sequentially, moisture values for each of these zones. Also included on the web is a moisture profiler for controlling the amount of moisture in the zones which has a response time much faster than the time required for a single cross direction scan by the scanning moisture sensor.

The method comprises the steps of measuring the amount of moisture in each of the zones substantially continuously by the use of a fixed moisture sensor located at each of the zones. The measured moisture by the fixed sensor is calibrated by comparing this measurement with the moisture value from the scanning moisture sensor to provide a calibration constant. Then, by utilizing the calibration constant the measured moisture is corrected from the fixed sensor to control the moisture profiler.

BRIEF DESCRIPTION OF DRAWINGS

FIG. 1 is a block diagram showing the overall apparatus with which the method of the present invention is used.

FIG. 2 is a cross sectional view of a nonscanning moisture sensor illustrated in FIG. 1.

FIG. 3 is a simplified plan view illustrating the nonscanning moisture sensor of FIG. 1 and its communication connection to the remaining processing units of FIG. 1.

FIG. 4 is a plan view of one side of a printed circuitboard used in the moisture sensor of FIG. 2.

FIG. 5 is a plan view of the other side of a printed circuitboard of the moisture sensor used in FIG. 2.

FIG. 6 is a side view, simplified somewhat, of the printed circuitboard of FIGS. 4 and 5, showing the circuit pin connectors.

FIG. 7 is a circuit schematic of the nonscanning moisture sensor of FIG. 2.

FIG. 8 is a flow chart used in performing the method of the present invention.

DETAILED DESCRIPTION OF PREFERRED EMBODIMENT

As illustrated in FIG. 1, an object of the present invention is to control the moisture in the various slices or zones of the paper 10 being manufactured, for example, by a papermaking machine, which is moving in a machine direction, indicated by the arrows 11. As is well known in the papermaking process, in addition to removing gross amounts of moisture from the paper being manufactured to bring it to the desired quality level, it is also necessary to remove moisture streaks. These commonly occur in the machine direction—perhaps over a width of one or two zones or slices. To accomplish this purpose a moisture profiler 12 is utilized which consists of a series of heating modules with quartz heating elements as illustrated in the above U.S. Pat. No. 4,573,402.

Furthermore, a typical way of measuring the moisture is by the use of the scanning moisture sensor 13, which includes a pair of scanning heads 14 which, for example, every 30 seconds scan in a cross direction across the paper (perpendicular to machine direction 11) and provide by the use of a pair of infrared light beams in a manner well known the sequential measurement of the moisture value of each zone or slice. Normally, the output of scanning moisture sensor 13 is coupled via line 16 to a process control system 17, and then via a cross direction link unit 18 and interface unit 19 to normally drive the moisture profiler 12 (and also a steam drum, not shown). However, as discussed above, if a fast response time is desired, this is very difficult to accomplish merely with the use of the scanning moisture sensor 13 which must scan across the sheet and in order to provide for proper calibration must go off sheet. Thus there is a time lapse of perhaps 30 seconds. This is very critical, especially where sheet material such as linerboard is being manufactured. Here, as little as a two second response time is desired. This is the time from which an unwanted moisture streak is sensed to the time when the moisture profiler 12 corrects this moisture streak by applying heat to that particular zone where the streak occurs. And a moisture profiler 12 of the type using electrical quartz heating elements inherently has the required faster response time.

Thus, in accordance with the method of the present invention there is provided a nonscanning or fixed moisture sensor 21 which, since it has a measuring element for each zone or slice of paper 10, in essence continuously provides a measurement $S_i$ on the line 22 of the moisture in the various zones of paper 10. However, as discussed above, its accuracy is not as good as the scanning moisture sensor 13. Thus, the nonscanning or fixed sensor 21 cannot be utilized on a stand alone basis. The measured moisture output $S_i$ on line 22 is coupled into a sensor support unit 23, which in turn is connected to a cross direction network 24. The cross direction network, as discussed previously, is the network for the signal $M_i$ of the scanning moisture sensor 13, and interfaces with the process control system 17, the interface unit 19 of moisture profiler 12 and in addition, the cross direction operation center Unit 26.

The structural details of nonscanning moisture sensor 21 are more fully illustrated in the enlarged cross direction of FIG. 2 which includes the sensor frame 31 carrying a sheet guide 32, below which the paper 10 moves in the direction 11. A moisture sensing unit 33 is indicated, which will be described in detail in the subsequent figures, which is mounted between a front wear strip 34 and rear wear strip 36. In general, a moisture sensing unit 33 presents a flat, smooth surface to the moving paper 10. In front of alternate units is a temperature sensor 37 used in the temperature compensation and linearization process.

FIG. 3 illustrates the array of temperature sensor units 33 which extend substantially across the sheet. Each sensor 33 is connected via both a data bus 40 and address bus 42, along with the temperature sensor outputs from the units 37, to the sensor support unit 23 and then to the cross direction network bus 24. Information from each sensor unit 33 is obtained in a manner well known in the data processing art, by scanning across each sensor unit by addressing it on bus 42 and then reading out the data on bus 40. Since this is done by the high speed sensor support unit 23 which includes a typical microprocessor, in effect the amount of moisture being measured in each zone is a continuous measurement. That is the scanning time for the total cross direction of a sheet is in milliseconds.

The moisture sensing unit 33, indicated in FIG. 2, is basically composed of a printed circuit board illustrated in FIGS. 4, 5 and 6. The board 41, as illustrated in FIG. 4, is plated on the side facing the paper with transmit and receive capacitive electrodes of which the paper forms a part of the dielectric of the capacitor. The value of the capacitance $C_x$ is proportional to the amount of moisture in the paper.

Then on the opposite side of the printed circuitboard 41, as illustrated in FIG. 5, are additional reference and ground electrodes to complete the moisture measuring unit. FIG. 6 illustrates the various pin electrodes used to connect the above printed electrodes.

FIGS. 4, 5, and 6 are illustrated in simplified form in FIG. 7 which shows the actual electrical connections along with the effective capitance which exists in the circuit. Referring to the top of FIG. 7, there is the paper 10 which is illustrated and which has the capacitance $C_x$ illustrated by the dashed capacitor. Then the moisture sensing element is illustrated at 33 with a printed circuitboard at 41, which has its top surface the transmit and receive electrodes so designated being potted by an epoxy dielectric layer 45 to provide a smooth surface. Each receive electrode is surrounded by a pair of transmit electrodes which are connected to the transmit line 43 driven by an oscillator 48. The receive line 44 on which the signal (Sig) is produced is connected to the receive electrode 44. The other electrical output of sensor unit 33 is an electrical connection designated reference (Ref) to a reference electrode 46 which is on the backside of printed circuitboard 41, as previously illustrated in FIG. 5. In addition, there are a pair of surrounding ground electrodes or planes 47. The representations of the electrodes and their configurations in FIG. 7 are simplified; thus FIGS. 4 and 5 must be referred to.

Very specifically and referring to FIG. 5, the reference electrode for each sensing unit consists of four vertical plated areas 46 which lie in the center of the four receive areas with which they are juxtaposed (FIG. 4). And then the ground plane, or conductor 47, is deposited or plated on the remaining portion of the back of circuitboard 41 to provide an effective shield or isolation for the transmit receive capacitive electrodes. That is, referring to FIG. 2, this ground plane isolates the measuring elements from the remainder of the circuitry above it. The circuitry includes that shown in the remainder of FIG. 7.

A source of electrical energy is provided by the oscillator 48 which provides a signal of amplitude A having a frequency of, for example, 500 kilohertz. This is coupled via the transmit line 43 to the transmit electrodes. And then through a ground on the receiving line 44 and capacitor $C_6$ the signal path is completed back to oscillator 48. Between the capacitive electrodes of the transmit and receive units, in addition to the capacitance $C_x$ of the moisture carrying paper, there is the air capacitance $C_1$, $C_2$ in the dielectric epoxy layer 42, $C_3$ in the printed circuitboard 41, $C_4$ between the reference and transmit electrodes and the capacitance $C_0$ between the transmit electrode and the ground plane 47. The reference line is grounded through the external capacitance $C_g$. Only representational capacitances have been shown and of course, the same would occur between the other transmit and receive plates, as for example, $C_1$, $C_2$ and $C_3$. Thus, the indicated capacitors are intended to represent the entire capacitance of the particular moisture sensing unit 33.

The signals from the reference and signal lines are differenced in a unit 49 and synchronously demodulated at 52 to provide the measured moisture $S_i$ at the output 53. This is coupled via amplifier 54 to multiplexer 56, which might typically be part of the sensor support unit 23. Then the output of this is sent to the cross direction net 24.

In order to provide the signal $S_i$ that represents moisture content in paper 10, the signal must faithfully indicate the value of the capacitance $C_x$. Thus, the other capacitance values must be standardized or cancelled out and any temperature drift must be compensated for. It is noted that the capaciter $C_4$ is proportional to $C_2$ plus $C_3$ for all temperatures.

The equations page following this description illustrates how the differencing of the reference and signal outputs of the moisture sensor 33 by unit 49 provides a signal representing capacitance $C_x$ in paper 10 and thus an indication of moisture content of that paper for the particular zone over which the moisture sensing element is located.

In equations 1 and 2, the electrical signals designated "Ref" and "Sig" are shown as being dependent on twice the amplitude A, the oscillator output, and the combination of the various capacitors illustrated in FIG. 7.

Equations 3 and 4 are rearrangements of equations 1 and 2. Then by assuming the conditions of equations 5 and 6, equations 3 and 4 simplify into equations 7 and 8. Then in equation 9, a choice of the value of the capacitor $C_g$ (which is on the reference line of FIG. 7) is made so that the ratio of $C_4$ to $C_g$ is approximately equal to the ratio combination illustrated in the equation. From a practical standpoint, this is done by measuring the signal output with no paper in the gap of the capacitive electrodes and then bringing the signal $S_i$ to '0.' Note that, as discussed above, $C_4$ varies with temperature in the same manner as $C_2$ and $C_3$. Thus choosing this ratio cancels out or effectively tracks the temperature variation.

Finally, equation 10 is the result of the operation of the differencing unit 49, subtracting the reference from the signal, to produce a signal $S_i$ which is the ratio of the paper capacitance $C_x$ and the external capacitance $C_g$ on the signal line. The addition of the external capacitance $C_g$ and its adjustment provides a desired null signal as illustrated by equation 9 to cancel out the effects of the other electrode capacitances.

The overall method is illustrated by the flow chart of FIG. 8 where, in the step 61, the amount of moisture $M_i$ in each of the zones is measured by the scanning sensor at zone i. And then in step 62 the moisture signal $S_i$ is also measured by the fixed sensor. Then the $S_i$ signal is temperature compensated and linearized, as shown in step 63, by sensing the temperature $T_i$ at that zone by the associated temperature sensor 37 (see FIGS. 2 and 3) and by using the signal value $S_o$ measured with no paper near the sensor; this is achieved by actually lifting the sensor from the paper. In step 64 a calibration constant is calculated by comparing the signal value $X_i$ with the scanning sensor value, $M_i$, to provide a calibration constant, $K_i$. Since it is assumed that the scanning moisture sensors are much more accurate than the fixed or nonscanning moisture sensor, this is in essence an error correction factor.

The above calibration constant, $K_1$, for this particular zone is stored and then in step 66 for subsequent zones in time and in the same machine direction moisture $MOI_i$ is determined by taking the linearized compensated value of $S_i$, that is, $X_i$, and multiplying it by the calibration constant $K_i$ as illustrated. This final corrected value is then used in the interface unit 19, FIG. 1, to drive the moisture profiler 12, as shown in step 67.

Since scanning unit 13 is being used to calibrate fixed sensor 21, the two sensors should be located close enough, e.g., 1 foot, so there is no appreciable change in moisture. However, a uniform or predictable change can be easily compensated.

Thus, the present invention has provided a moisture control method which has a rapid response to change of moisture content in, for example, linerboard. This has been achieved with high accuracy by linking of the nonscanning moisture sensor with the scanning moisture sensor in the manner described above. In addition, the nonscanning moisture sensor itself has improved operation due to the cancelling out of the effects of various stray capacitances by the differencing technique and the electrode arrangement.

EQUATIONS $$Ref = 2A \left( \frac{1}{1 + C_g/C_4} \right) \quad (1)$$

$$Sig = 2A \left( \frac{1}{1 + \frac{C_6}{C_x + C_1 + C_2 + C_3}} \right) \quad (2)$$

$$Ref = 2A \left( \frac{C_4}{C_g + C_4} \right) \quad (3)$$

$$Sig = 2A \left( \frac{C_x + C_1 + C_2 + C_3}{C_x + C_1 + C_2 + C_3 + C_6} \right) \quad (4)$$

$$C_g >> C_4 \quad (5)$$

$$C_6 >> C_x + C_1 + C_2 + C_3 \quad (6)$$

$$Ref \simeq 2A \left( \frac{C_4}{C_g} \right) \quad (7)$$

$$Sig \simeq 2A \left( \frac{C_x + C_1 + C_2 + C_3}{C_6} \right) \quad (8)$$

$$\text{Choose } \frac{C_4}{C_g} \simeq \frac{C_1 + C_2 + C_3}{C_6} \quad (9)$$

$$\therefore Sig - Ref \simeq 2A \left( \frac{C_x}{C_6} \right) \quad (10)$$

I claim:

1. A method using a fixed moisture sensor for controlling the amount of moisture that is associated with a web of moving material where a scanning moisture sensor scans across zones or slices of said web in a cross direction (CD) perpendicular to the machine direction of movement of said web to provide, sequentially, moisture values for each of said zones and also including a moisture profiler for controlling said amounts of moisture in said zones and having a response time much faster than the time required for a single cross direction scan by said scanning moisture sensor, said method comprising the following steps:
   measuring the amount of moisture in each of said zones substantially continuously by use of a said fixed moisture sensor located at each zone;
   calibrating said measured moisture by said fixed sensor by comparing with a said moisture value from said scanning moisture sensor to provide a calibration constant;
   and utilizing said calibration constant by correcting said measured moisture from said fixed sensor to control said moisture profiler.

2. A method as in claim 1 where said fixed moisture sensor includes capacitive electrodes and a juxtaposed reference electrode and where said step of measuring said amounts of moisture by said fixed sensor includes the step of differencing signals from said capacitive electrodes and said reference electrode.

3. A method as in claim 2, including the step of adding external capacitance to said reference electrode to provide a null signal.

4. A method as in claim 2, including the step of providing a ground plane for said capacitive electrodes for electrical isolation.

5. A method as in claim 3 where said external capacitance is ratioed against a reference electrode to capacitive electrode capacitance which varies with temperature proportionately with the capacitance of said capacitive electrodes themselves.

* * * * *